(12) United States Patent
Wingler et al.

(10) Patent No.: US 7,637,904 B2
(45) Date of Patent: Dec. 29, 2009

(54) CATHETER WITH SNAP ON FEATURE

(75) Inventors: Troy W. Wingler, Gosport, IN (US);
Rodney W. Bosley, Jr., Bloomington, IN (US); John H. Ward, Bloomington, IN (US); J. Michael Putman, Dallas, TX (US); Scott K. Philhower, Bloomington, IN (US); Bruce J. DeMars, Bloomington, IN (US); Gregory A. Frankland, Unionville, IN (US)

(73) Assignee: Vance Products Incorporated, Spencer, IN (US)

( * ) Notice: Subject to any disclaimer, the term of this patent is extended or adjusted under 35 U.S.C. 154(b) by 883 days.

(21) Appl. No.: 10/741,918

(22) Filed: Dec. 19, 2003

(65) Prior Publication Data

US 2005/0137448 A1 Jun. 23, 2005

(51) Int. Cl.
*A61M 25/16* (2006.01)
(52) U.S. Cl. ..................................... 604/533
(58) Field of Classification Search ................ 604/167, 604/263, 236, 523–536, 905, 284
See application file for complete search history.

(56) References Cited

U.S. PATENT DOCUMENTS

| | | | |
|---|---|---|---|
| 4,023,559 A * | 5/1977 | Gaskell | 600/572 |
| 4,401,124 A | 8/1983 | Guess et al. | |
| 4,533,345 A | 8/1985 | Louw | |
| 4,863,423 A | 9/1989 | Wallace | |
| 4,865,589 A | 9/1989 | Simmet et al. | |
| 4,877,033 A | 10/1989 | Seitz, Jr. | |
| 5,081,997 A | 1/1992 | Bosley, Jr. et al. | |
| 5,085,636 A * | 2/1992 | Burns | 604/99.04 |
| 5,147,315 A | 9/1992 | Weber | |
| 5,195,979 A | 3/1993 | Schinkel et al. | |
| 5,201,314 A | 4/1993 | Bosley et al. | |
| 5,217,466 A | 6/1993 | Hasson | |

(Continued)

FOREIGN PATENT DOCUMENTS

EP 0 456 342 11/1991

(Continued)

OTHER PUBLICATIONS

Engage Polyolefin Elastomer Product Chart dated Sep. 1998.

(Continued)

*Primary Examiner*—Manuel A Mendez
(74) *Attorney, Agent, or Firm*—Brinks Hofer Gilson & Lione

(57) ABSTRACT

An embryo transfer catheter with a protective sheath is disclosed. The use of a protective sheath shields a guide catheter from cervical mucus. The retracted open flaps of the outer protective sheath draw the mucus and blood away from the inner guide catheter. This allows an inner embryo transfer sheath to enter the uterus unobstructed. The embryo is then transferred to the uterus by means of fluid pressure with a culture medium. The protective sheath may be snap fit onto the guide catheter. The sheaths and catheters may be manufactured in a variety of lengths for individual convenience and then snap-fit onto each other for better control during an embryo implantation procedure. Other catheters and related instruments may also be manufactured with snap-on features.

20 Claims, 7 Drawing Sheets

U.S. PATENT DOCUMENTS

| | | | |
|---|---|---|---|
| 5,259,837 A | 11/1993 | Van Wormer | |
| 5,273,527 A | 12/1993 | Schatz et al. | |
| 5,289,831 A | 3/1994 | Bosley | |
| 5,290,303 A | 3/1994 | Pingleton et al. | |
| 5,360,242 A * | 11/1994 | Argent | 285/330 |
| 5,360,389 A | 11/1994 | Chenette | |
| 5,472,419 A | 12/1995 | Bacich | |
| 5,486,191 A | 1/1996 | Pasricha et al. | |
| 5,611,345 A | 3/1997 | Hibbeln | |
| 5,724,977 A | 3/1998 | Yock et al. | |
| 5,752,970 A * | 5/1998 | Yoon | 606/185 |
| 5,769,821 A | 6/1998 | Abrahamson et al. | |
| 5,772,643 A * | 6/1998 | Howell et al. | 604/533 |
| 5,795,325 A | 8/1998 | Valley et al. | |
| 5,797,888 A * | 8/1998 | Yoon | 604/530 |
| 5,843,023 A | 12/1998 | Cecchi | |
| 6,036,682 A | 3/2000 | Lange et al. | |
| 6,165,165 A | 12/2000 | Cecchi et al. | |
| 6,302,875 B1 | 10/2001 | Makower et al. | |
| 6,527,752 B1 | 3/2003 | Bosley, Jr. et al. | |
| 6,610,005 B1 | 8/2003 | Tao | |

FOREIGN PATENT DOCUMENTS

| | | |
|---|---|---|
| EP | 0 995 459 A2 | 4/2000 |
| EP | 1 149 598 A2 | 10/2001 |
| WO | WO 95/20418 | 8/1995 |
| WO | WO 96/40342 | 12/1996 |
| WO | WO 99/37348 | 7/1999 |
| WO | WO 01/21081 A1 | 3/2001 |
| WO | WO 01/74417 A2 | 10/2001 |

OTHER PUBLICATIONS

Search Report dated Mar. 4, 2004, for corresponding international application No. PCT/US03/31687.

* cited by examiner

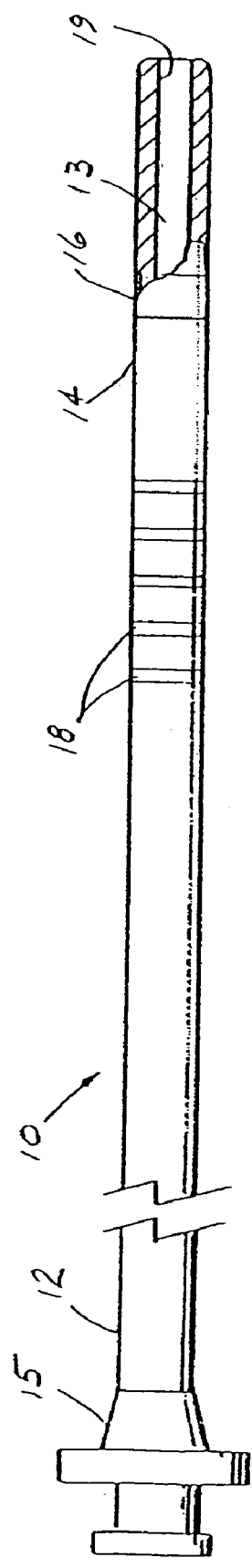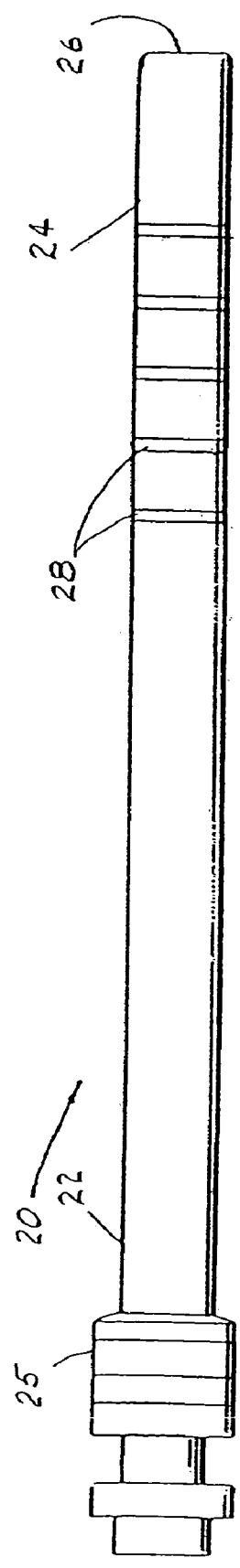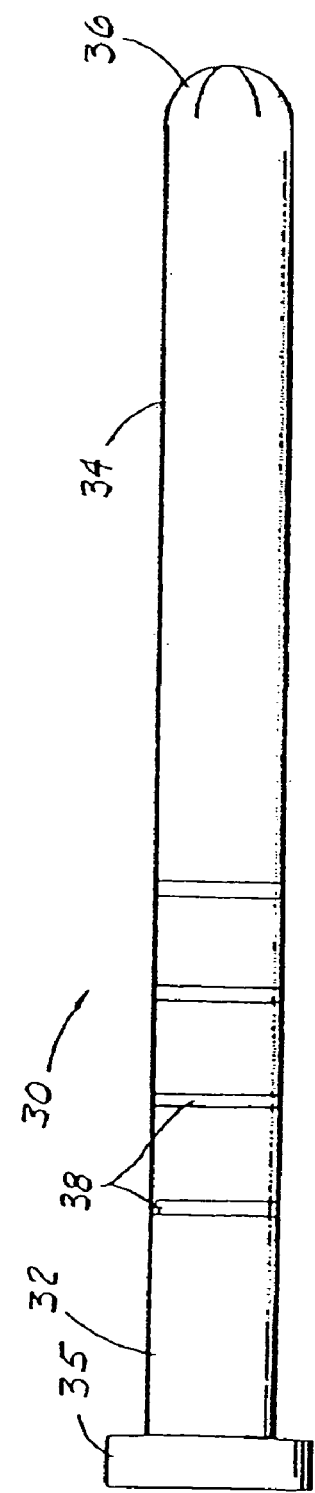

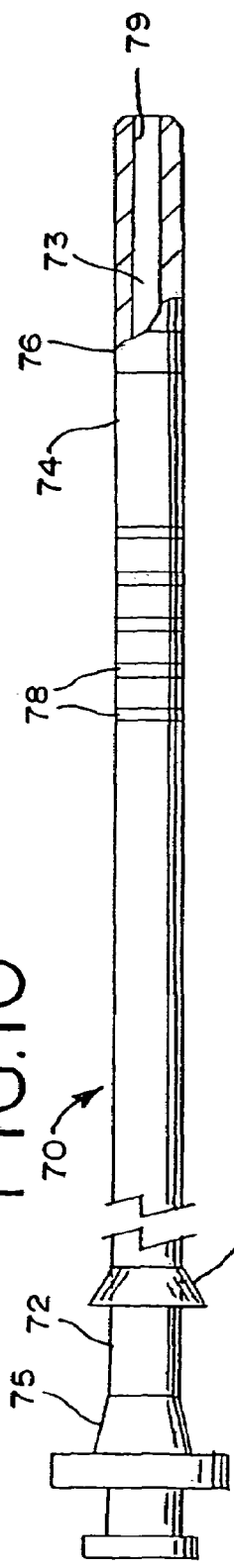
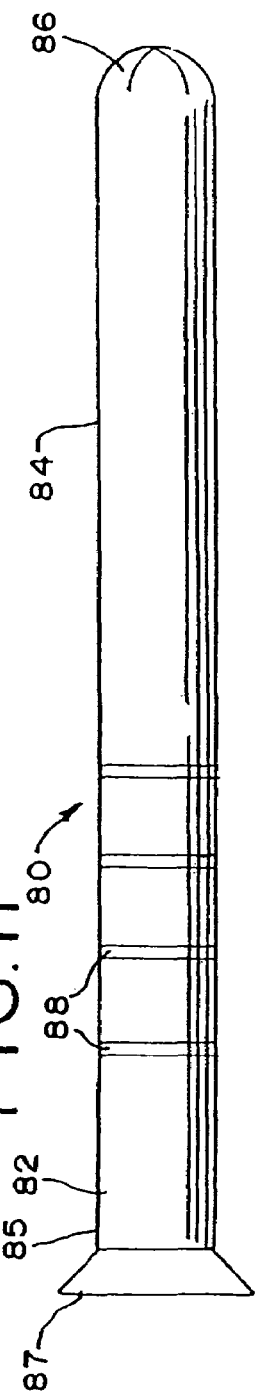
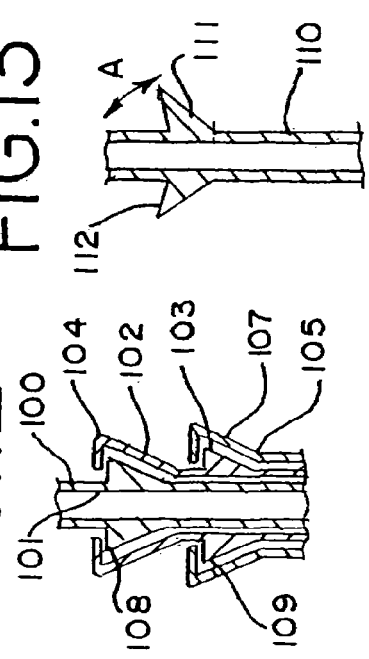
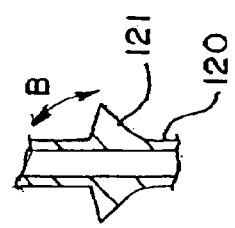
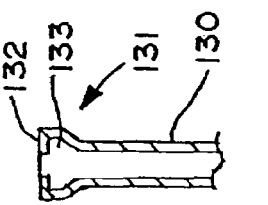
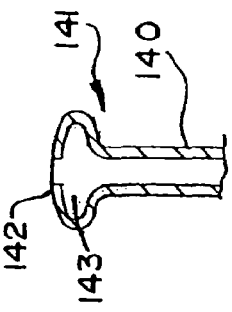

CATHETER WITH SNAP ON FEATURE

BACKGROUND OF THE INVENTION

Human In Vitro Fertilization (IVF) and Embryo Transfer (ET), first successfully performed in 1978, has become a widely practiced procedure to treat infertile couples who have failed with more conventional methods of therapy such as superovulation and intrauterine insemination. The most common indications for IVF and related procedures, such as Gamete In Vitro Fertilization or Gamete Intra-Fallopian Transfer (GIFT) which includes women having blocked or damaged fallopian tubes, and includes low sperm and/or egg quality. Related factors include age of the female, and the degree of endometrial receptivity. The procedure may also be used in cases of severe male factor where direct (intracytoplasmic) injection of sperm is an option. Another indication for the procedure is when the shell of the egg is abnormally thick, thus preventing the fertilized and dividing early embryo to escape and implant into the uterus. Creating a small opening through the shell has been shown to increase implantation rates. IVF is also being used when clinical or genetic factors require implantation of donor eggs from a fertile female that are fertilized in vitro and implanted into the recipient female using standard techniques.

The IVF/ET procedure typically involves the hormonal stimulation of the female to first suppress her ability to ovulate on her own, then stimulate development of follicles in the ovaries with a fertility medication. The mature eggs are removed from the ovary transvaginally using a needle, preferably guided under ultrasound. Following harvesting of the eggs, the eggs are identified and sorted with regard to maturity, and then placed with a sperm sample from the male. Approximately 24 hours after fertilization, the eggs are examined to confirm fertilization, which occurs in approximately 65% to 85% of the eggs harvested. After a short development period, the embryos are transferred, along with a volume of fluid, to the uterus using a delivery catheter. The delivery catheter is made of a soft plastic material to avoid damage to the endometrium.

There are many potential difficulties in achieving a successful implantation. Because of the soft nature of the standard delivery catheter, in a number of cases, the tip of the catheter may bend back on itself or curve away from the fundus of the uterus. The tip may also accidentally pass between the layer of the endometrium and myometrium. Conversely, a stiffer catheter increases the risk of trauma to the uterus or cervix, with the latter possibly leading to the release of prostaglandins and expulsion of the eggs from the endometrium.

One particular difficulty is the environment in which the catheters must function. Cervical tissue is mucousal, and the guiding catheter may become encumbered with mucus or blood when it passes through the opening of the cervix. As a result, the transfer catheter may become covered or clogged with mucus when it clears the guiding catheter. The mucus may then interfere with the transfer of the embryos, with the possibility of the embryos sticking to the mucus and not being transferred to the uterus. Other undesirable possibilities include subsequent transfer of embryos to the cervix or even to the vagina upon withdrawal of the catheters.

Several unsuccessful attempts have been made to improve success rates. U.S. Pat. No. 6,165,165 uses a guiding catheter and an implant catheter, the implant catheter made from materials of two different durometers, so that the stiffness of the catheter decreases from the proximal end to the distal end of the catheter. The resulting catheter may be easier to guide, but is still subject to interference from mucus. WIPO International Patent Applications WO99/37348 and WO01/74417 attempt to solve the problem with an end cap on a guiding catheter that swings open to allow the transfer catheter to pass through an opening and transfer the embryos. Alternatively, the transfer catheter may have a side port rather than an axial port on the distal end, so the side port will avoid interference from mucus. These embodiments are still subject to interference from mucus.

One way to increase the likelihood of success is to tailor the catheters used to the person undergoing the treatment, i.e., by using different lengths of catheter. These attempts to tailor the catheters have led to a proliferation of lengths of catheters, especially in guide catheters. Even with overnight delivery of the desired resources, this results in the need for hospitals and clinics to inventory more catheters and more sets of catheters than is desirable. In addition, these procedures are recognized as being very expensive. While catheters are not a major component of the cost of these procedures, anything that can help control their very expensive costs will be welcome. What is needed is a catheter system that can accomplish embryo implantation while helping to minimize costs and without the need for carrying many lengths of catheter sets.

What is needed is a catheter system that can increase the likelihood of successful embryo implantation patients desiring this procedure without interference from mucousal matter. What is also needed is a catheter system in which the catheter length may be varied without undue cost penalties.

BRIEF SUMMARY OF THE INVENTION

One aspect of the invention is a cellular material transfer system. The system comprises three coaxial catheters, an inner transfer catheter, a guide catheter for holding a guiding the transfer catheter, wherein a distal end of the protective sheath is opened by advancing the guide catheter or by retracting the protective sheath, and opening flaps of the protective sheath draw mucus and blood away from the guide catheter.

Another aspect of the invention is a method of implanting cellular material in a uterus. The method comprises passing an assembly through an opening in a cervix, the assembly including a protective sheath, a guide catheter, and a delivery catheter. The method also comprises advancing at least one tip of the assembly to an internal ostium of the cervix, and retracting the protective sheath to expose the tip of the guide catheter thereby opening flaps of the protective sheath and drawing mucus and blood away from the guide catheter. The method also comprises advancing the delivery catheter through the guide catheter and transferring cellular material from the transfer catheter into the uterus.

Another aspect of the invention is a cellular material transfer system. The cellular transfer system comprises a catheter and a hub, and a guide catheter for placing outside the transfer catheter, wherein the guide catheter is configured to snap fit onto the transfer catheter. Another aspect of the invention is a method of implanting an embryo in a uterus. The method comprises passing an assembly, the assembly including a transfer catheter, a guide catheter and a protective sheath, through an opening in a cervix. The method also comprises advancing the assembly to an internal ostium of the cervix, retracting the protective sheath and drawing mucus and blood away from the guide catheter. The method then comprises advancing the transfer catheter through the guide catheter and transferring the embryo from the transfer catheter to the uterus.

Another aspect of the invention is a method for collecting a sample. The method comprises passing an assembly through an opening in a body, the assembly including a protective sheath, a guide catheter, and a sampling catheter. The method also comprises advancing the assembly to a desired point in the body and retracting the protective sheath to expose a tip of the guide catheter. The method then comprises advancing the sampling catheter through the guide catheter, passing the sampling catheter through the guide catheter, and aspirating the sample. Another aspect of the invention is a catheter system, the system comprising a first catheter having a snap on feature and a second catheter.

Another aspect of the invention is a system for sampling a body fluid, the system comprising a sampling catheter, a guide catheter holding the sampling catheter; and a protective sheath outside the guide catheter. Yet another aspect of the invention is a cellular transfer catheter system, comprising a first catheter having a snap on feature and a second catheter.

Another aspect of the invention is a cellular transfer system comprising a transfer catheter, a guide catheter for holding and guiding the transfer catheter, and a protective sheath outside the guide catheter. The protective sheath comprises at least one of break-through and peel-away features, wherein the protective sheath splits into at least two portions when the protective sheath is withdrawn or the guide catheter is advanced through the protective sheath.

There are many ways to practice the present invention, a few of which are shown in the following drawings and specification. The embodiments described below are not meant to limit the invention, but rather to describe and illustrate the many ways that the present invention may be used.

BRIEF DESCRIPTION OF SEVERAL VIEWS OF THE DRAWINGS

FIG. 1 depicts a plan view of an transfer or delivery catheter.

FIG. 2 depicts a plan view of a guide catheter.

FIG. 3 depicts a plan view of a protective sheath.

FIGS. 10-11 depict a two-catheter snap fit system.

FIGS. 12-16 depict cross-section view of several snap on features.

DETAILED DESCRIPTION OF THE PRESENTLY PREFERRED EMBODIMENTS OF THE INVENTION

Figure 4:
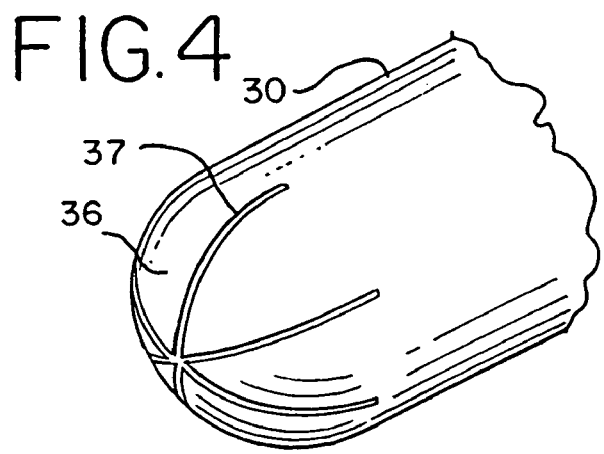
FIG. 4 depicts a perspective view of the distal end of the embodiment of FIG. 3.

FIGS. 1-3 depict a cellular material transfer catheter system that comprises three catheters, an inner transfer catheter 10, a guide catheter 20, and an outer protective sheath 30. The transfer catheter 10 extends somewhat longer than the guide catheter 20, and the protective outer sheath 30. The inner catheter, transfer catheter 10, includes a passageway 13 of sufficient diameter to hold and deliver cellular material, such as early embryos, gametes (oocyte or sperm), blastocysts, or zygotes that are to be transferred from in vitro culture for in vivo implantation and/or fertilization.

The cellular material or embryo transfer catheter 10 includes a proximal portion 12 and a distal portion 14. The proximal portion may include a hub 15 for interfacing with a syringe for implanting cellular material. The catheter may also include an echogenic tip 16, preferably made of stainless steel, for detecting the distal end via ultrasound. The catheter may also have markings 18 at the proximal or distal end indicating a position of the catheter to implantation personnel. The catheter itself is made of relatively soft material, such as polyethylene. Other materials that may be used include urethane, polyolefin, polyamides, fluoropolymers including but not limited to polytetrafluoroethylene, and silicone.

The diameter of the passageway and volume of the fluid and material contained therein is preferably minimized to a diameter of no greater than 0.025", preferably less than 0.023", and most preferably between 0.018" and 0.021". The transfer volume is no greater than 30 μl, more preferably 20 μl or less, and most preferably between 5 and 15 μl. Clinical experience with this catheter, for IVF/ET having a 0.020" diameter with a volume of approximately 10 μl, indicates an unexpected increase in pregnancy rates, possibly due to the reduced amount of fluid delivered with the embryos. The reduced transfer volume ostensibly lessens the tendency of embryos to migrate to another section of the uterus, for instance, into the fallopian tubes. By increasing the implantation rate, fewer embryos may be needed, thereby reducing the number of unwanted multiple pregnancies and further risks.

FIG. 2 depicts a guide catheter 20 used coaxially with transfer catheter 10. The guide catheter 20 is of relatively simple construction, and may comprise a proximal portion 22 and a distal portion 24, and distal end 26. The distal end 26 is preferably open rather than closed. The catheter 20 also comprises a hub 25 for interfacing with the embryo transfer catheter 10, and possibly the protective sheath 30. The guide catheter may also comprise markings 28 at the distal portion 24 to guide delivery personnel. The guide catheter is preferably somewhat stiffer than the embryo transfer catheter. Materials suitable for the guide catheter are many, so long as the guide catheter is able to hold its shape without drooping or sag during the implantation procedure. Materials which have been used include fluoropolymers such as polytetrafluoroethylene (PTFE), although other materials, as mentioned above, may also be used.

The outer protective sheath 30 of FIG. 3 is also of relatively simple construction. It has a proximal end 32, a distal end portion 34 with a distal end 36 and may have a hub or interface 35. The sheath may be made with markings 38 for guidance of delivery personnel. The protective sheath is also relatively stiff compared to the embryo transfer catheter. It is important that the guide catheter and the protective sheath be dimensionally stable (do not sag) so that operating personnel may control the exact position of the catheter and the sheath during implantation procedures. The inner transfer catheter should be relatively soft so as to avoid any damage to delicate tissues in the uterus.

The transfer catheter, the guide catheter and the protective sheath catheter are used to implant an embryo into a uterus of a woman. As discussed above, one problem with such implantations is fouling of the distal end of the transfer catheter. The mucousal nature of the cervix, and the presence of mucus and blood, makes the problem an inherent one for any procedure in this area of the body. The present invention solves the problem in the following manner. The three catheters are advanced as a unit through the vagina, through the cervix, and positioned at the internal cervical ostium. The echogenic tip and the markings on one or more of the catheters assist in this operation.

The protective sheath, with the guide catheter still inside the protective sheath, is then retracted to expose the tip of the guide catheter. The distal end of the protective sheath is closed and is impervious to the fouling substances in the cervix, but the protective sheath is also scored or weakened so that the guide catheter is easily advanced through the scored or weakened end portion of the protective sheath. The protective sheath is designed to snap onto the guide catheter when completely retracted. The protective sheath at this point may be covered with mucus or blood or other fouling substances. In practice, these substances cling to the sheath while the guide catheter advances relatively free of the mucus and blood. It is not necessary to retract the protective sheath a great distance; about 1 to 2 cm is sufficient to clear the guide catheter and pull mucus and blood away from the guide catheter tip.

While most of the mucus and blood are retained on the protective sheath, a small amount may cling to the distal (protruding) end of the guide catheter. In practice, this small amount tends to cling to the sides of the guide catheter, rather than the area of the central lumen of the guide catheter. Thus, by extending the guide catheter through the protective sheath, a passageway that is free of fouling substances, such as mucus and blood, is cleared through the central lumen of the guide catheter. All that remains is to advance the transfer catheter through the guide catheter, and to implant the embryo or cellular material. As stated above, the transfer catheter preferably has an echogenic tip to guide operating personnel as to its exact position and to complete the transfer procedure for the embryo or other cellular material. It is preferable to use a syringe and to expel the embryo into the uterus by means of fluid pressure.

In one illustrative embodiment, the protective sheath has an outer diameter of about 6.8 Fr (about 2.27 mm) and has an overall length of about 11 or 16 cm. The guide catheter has an outer diameter of 4.7 Fr (1.57 mm) and an overall length of about 12 or 17 cm. The inner catheter diameter is about 0.483 mm with a length of approximately 19 or 24 cm. The delivery or transfer catheter extends approximately 5 cm beyond the tip of the guiding catheter, and the guide catheter extends about 1 to 2 cm beyond the tip of the protective sheath catheter. As mentioned above, optional graduated markings 18, 28 can be placed about the distal portion 142 of the delivery catheter 10 or the distal portion 24 of the guiding catheter 20 to determine the depth of penetration into the uterus or the amount of delivery catheter 10 that is exposed beyond the distal tip 26 of the guiding catheter 20. Additional graduated markings may also be placed on the guide sheath if desired.

Figure 5:
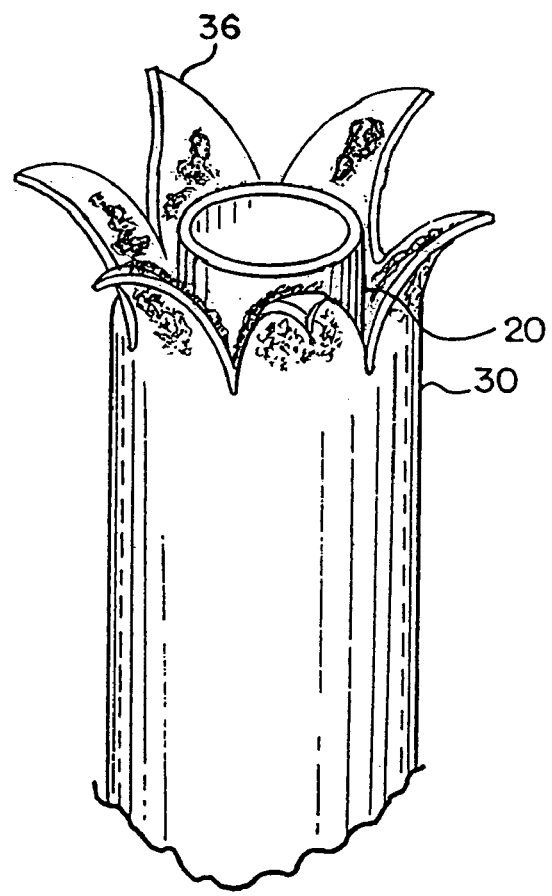
FIG. 5 depicts a perspective view of cooperation between the guide catheter and the protective sheath.

It is important that the guide catheter 20 be able to protrude through the protective sheath 30. Accordingly, the protective sheath is preferably penetrated, scored or provided with pull-away portions as illustrated in FIGS. 4-5. FIG. 4 is a perspective view protective sheath 30 with distal portions 36. The sheath is provided with several penetrations 37. The material is weakened in several places, such as with 5 or 6 penetrations in a star pattern, so that the distal portions 36 pull away and guide catheter 20 can easily maneuver through the distal end of protective sheath 30. A penetration is provided when material is removed, as shown in FIG. 4. A score is a series of penetrations or perforations, rather than a continuous, longer portion where material is removed.

FIG. 5 depicts a perspective view of guide catheter 20 emerging from protective sheath 30, or alternatively, protective sheath 30 being retracted around guide catheter 20. The end of the protective sheath is split into several now-discrete distal portions 36, which pull apart and draw mucus and blood away as the guide catheter emerges from the protective sheath. FIGS. 4-5 depict a star pattern, but other patterns are also possible. As mentioned above, this break-through feature may be provided by means of penetrations or perforations in the distal tip of the protective sheath.

Figure 6:
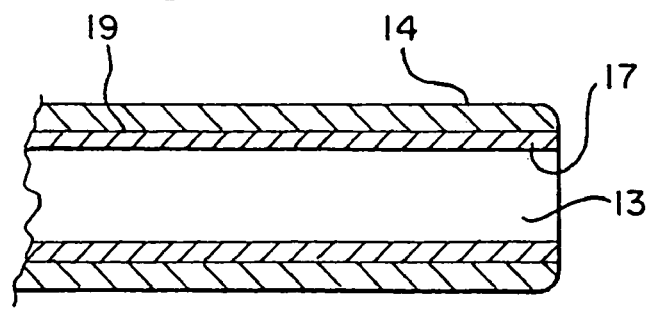
FIG. 6 depicts an alternative embodiment of a transfer or delivery catheter.

Because the delivery catheter is preferably made of a softer (lower durometer) polymer the surface energy density is usually higher, making the embryo more likely to adhere to the inner luminal surface. This is especially critical with a small lumen diameter, since with a typical embryo having a diameter of about 120 micrometers and a blastocyst having a diameter of about 260 micrometers, there is an increased likelihood of problems in delivery. Luminal surface treatments may help reduce friction for the smooth expulsion of oocytes and embryos. Ion beam bombardment is a well-known technique for reducing surface energy density of polymers. Polishing and surface coatings can also offer improvement in friction coefficients for otherwise "sticky" polymers. FIG. 6 depicts an embodiment in which the luminal surface 19 of the passageway 13 of the distal portion 14 of the delivery catheter is coated with lubricious material 17, such as parylene, to reduce surface energy density. Other coatings, such as PTFE, plasma or corona treatments, may also be used.

Figure 7:
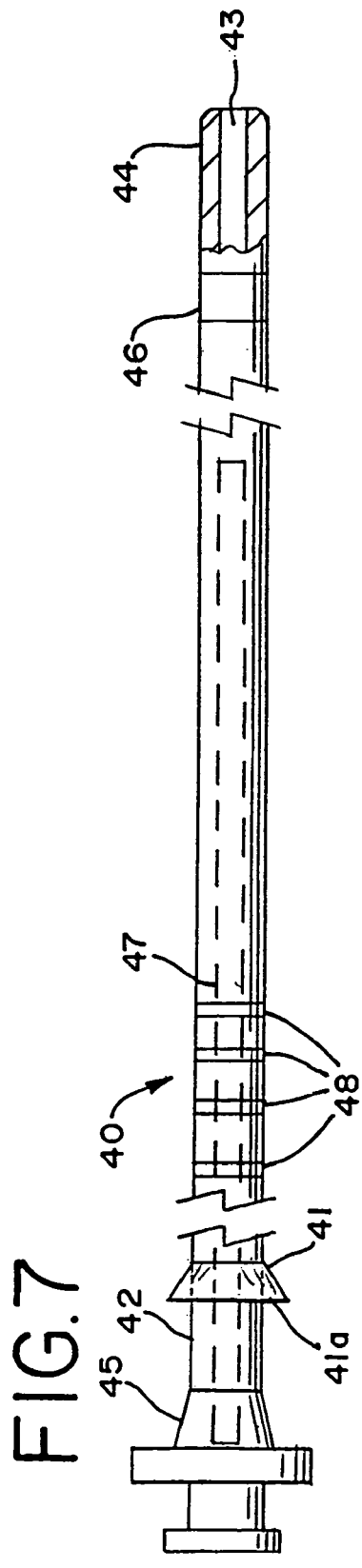
FIG. 7 depicts a reinforced transfer or delivery catheter with a male snap on feature.

In addition to the delivery catheter embodiment depicted in FIG. 1, the transfer catheter can be made with a stiffened proximal component. FIG. 7 depicts an embryo transfer catheter 40 having a stiffening or reinforcing portion 47 in its proximal portion 42. The embryo transfer catheter 40 also includes a central lumen 43 and a distal portion 44, preferably with an echogenic tip 46. The echogenic tip may be made of stainless steel, or may also take the form of particles embedded into the outer surface of the catheter. It has been found that spherically-shaped metallic particles are better for the resulting ultrasonic images. The particles are preferably incorporated into the desired location of the embryo transfer catheter, or possibly into the guide catheter, by molding them into the catheter.

The echogenic tip and the markings on one or more of the catheters assist in this operation. As stated above, the echogenic tip may be made of stainless steel, or may also take the form of particles embedded into the outer surface of the catheter. It has been found that spherically-shaped metallic particles are better for the resulting ultrasonic images. The particles are preferably incorporated into the desired location of the embryo transfer catheter, or possibly into the guide catheter, by molding them into the catheter. If a ring of stainless steel or other suitable material is used, it may be made echogenic by machining or otherwise placing on the surface grooves, bars, lines, bands, dimples, or other patterns which cause reflection, scattering and diffraction of ultrasound or other energy used to guide the surgeon in the placement of the catheter in the uterus.

The proximal portion 42 may also includes graduated markings 48 and an interface 45. Reinforcing member 47 may be a stainless steel tube that is bonded to the embryo catheter, preferably by heat or by an adhesive. However, the fit between the reinforcing member and the delivery catheter is typically sufficient that bonding is not required. The reinforcing member may be a cannula on the inside or on the outside of the transfer catheter. An example of a stiffened embryo transfer catheter is polyethylene tubing having a central lumen of 0.019 in (about 0.483 mm) diameter with a 23GXTW stainless steel cannula. An outer cannula, with polyethylene tubing on the inside of the cannula, may also be used.

The transfer catheter and the guide catheter are used to implant an embryo or other cellular material into a uterus of a woman. As discussed above, one problem with such implantations is the proliferation of sizes, especially of guide catheters. In one line of embryo transfer catheters, the lengths of transfer catheter may range from about 18.5 cm to about 23.5 cm, while the guiding catheters may range from 12 cm to 17 cm. Thus, in order to keep a reasonable inventory on hand, a hospital or clinic would necessarily stock a great number of kits, including variations in both the transfer and the guide catheters.

Using snap-fit features, the transfer catheter may be stocked separately from the guide catheter and from the protective sheath. The proper length of transfer catheter may then be selected, and the desired length of guide catheter may also be selected, independently of each other. If the available transfer and guide catheters use snap-fit features, the fit between the two may be insured and the physician conducting the embryo transfer procedure need not worry about controlling the movement of the catheters. This is also holds for the protective sheath, which may also be available in more than one length.

Another aspect of these embodiments is that almost any desired length of transfer catheter is interchangeable with almost any desired length of guide catheter. This interchangeability has been achieved without the use of a fitting to accomplish the interface, such as Luer lock fittings or other fittings that are costly to incorporate. This should lower the cost of manufacture of the catheters, as well as limit the number of parts and kits that must be stocked.

Transfer catheter 40 with proximal portion 42 also includes a male snap on or snap fit feature 41. This feature is a protrusion on an external surface of catheter 40. Snap fit feature 41 has an edge 41a facing the proximal direction, so that edge 41a may interface with a female snap fit or snap on feature on a mating part, such as guide catheter 50 in FIG. 8. Using the snap fit or snap on features, guide catheter 50 may be snap fit over delivery catheter 40. Guide catheter 50 includes a hub 55 at its proximal end and a female snap fit or snap on feature 59. Catheter 50 also has a central lumen 56 and may have marking bands 58 preferably at distal end 54. Catheter 50 has one or more ribs 53 and a reinforcing band 57 which may include connecting hub 55 around the proximal end. The band may be made of any desired, relatively stiffer material suitable for the application, such as PTFE or polyolefin.

Figure 9:
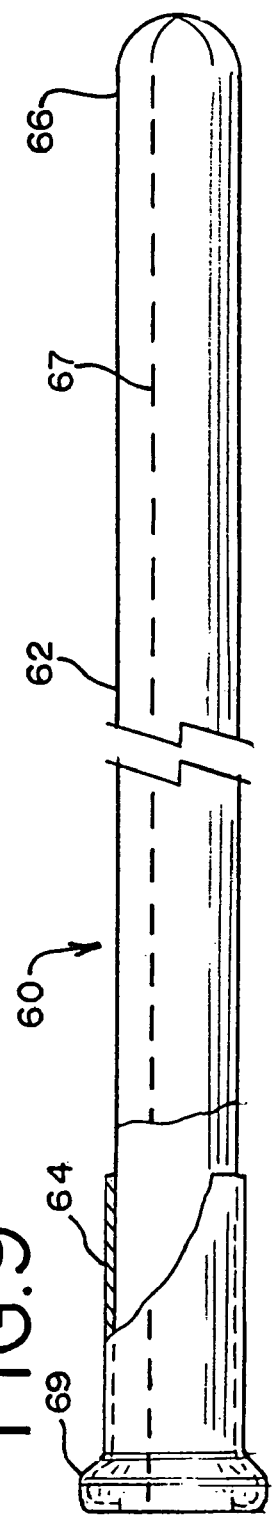
FIG. 9 depicts an alternative embodiment of a protective sheath with a female snap on feature and a peel-away feature.

Snap on feature 59 includes a space or void 59a for receiving male snap on feature 41 and an edge 59b for mating and interfering with edge 41a of the male snap on feature. The edges form an interference that prevents axial movement of the two components of which the edges are a part in a direction opposed to the direction that caused the engagement. That is, once catheter 40 is placed inside catheter 50, the snap fit features tend to prevent the removal of catheter 40 from catheter 50. Catheter 50 may also have a male snap on feature 51 for assembling protective sheath 60 to catheter 50. Protective sheath 60 in FIG. 9 may include a distal portion 62 with a distal end 66 which has been weakened and a reinforcing band 64 near its proximal end. Sheath 60 also has a female snap fit feature 69 for interfacing male snap fit feature 51 on guide catheter 50.

Protective sheath 60 may also have a score 67 marked at two locations 180° apart on its outer periphery. Score 67 is preferably used in conjunction with a polyethylene, polyurethane, PTFE or other fluoropolymer material for the outer sheath, so as to impart "peel-away" properties to the guide sheath. That is, when the three-catheter system is in place, the surgeon can withdraw outer sheath 60, or advance inner guide catheter 50. When distal end 66 is ruptured, the flaps open, retracting blood and mucus. When the rupture reaches scores 67, the scores also rupture, giving a peel-away effect, as protective sheath 60 essentially splits into two halves, drawing away the blood and mucus, and also removing protective sheath 60 from the area of interest. While the protective sheath has been described as having two scores 67, more than two scores may also be used to impart peel-away properties to the protective sheath. As discussed above with FIGS. 3-5, a score is a series of perforations or penetrations. PTFE may also be used without the scores as an inherent property of PTFE is to tear evenly when started at one end, and thus to strip away evenly.

Other features may assist in protecting the guide catheter and transfer catheter from fouling substances in the cervix. FIGS. 9a-9d depict embodiments of guide catheters and protective sheaths that feature a camming surface to urge the flaps of the protective sheath away from the distal end of the protective sheath before the guide catheter emerges. The camming surface is useful whether the guide catheter is advanced or the protective sheath withdrawn.

Figure 9A:
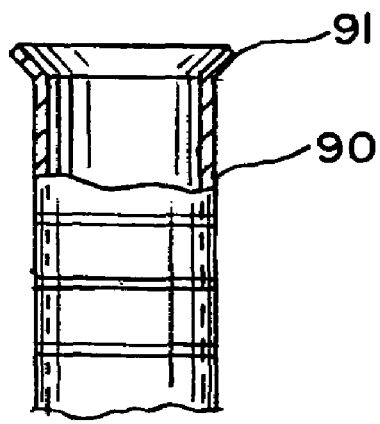
FIGS. 9a-9d depict alternate embodiments with a camming surface.

FIG. 9a depicts a guide catheter 90 with an external camming surface 91 for urging the apart the distal end of a protective sheath, such as protective sheath 30 in FIG. 3. As the guide catheter is advanced, or the protective sheath withdrawn, camming surface 91 of the guide catheter first contacts the inner portion of the distal end of the protective sheath, urging the flaps of the sheath apart, and with them, withdrawing the undesirable mucus and other material that may interfere with placement of the embryo.

Figure 9B:
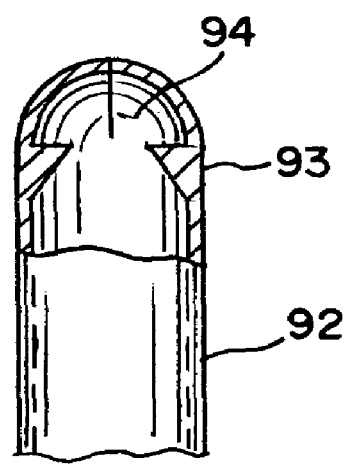
Figure 9C:
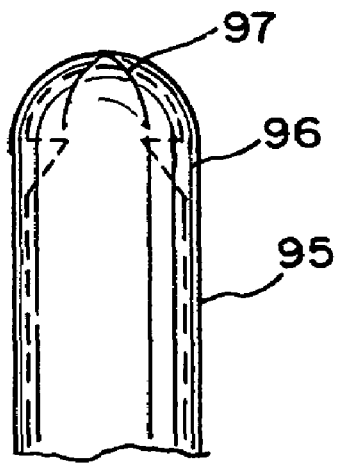

FIGS. 9b and 9c depict alternate embodiments, in which a camming surface is instead placed on the inner surface of the protective sheath. In FIG. 9b, protective sheath 92 is formed with an internal camming surface 93 for catching the distal tip of a guide catheter, such as guide catheter 20 in FIG. 2. Camming surface 93 receives the distal tip of the guide catheter, and urges apart the flaps 94 of the distal tip of the protective sheath. The camming surface is preferably thinned or aligned in coordination with the penetrations or cuts in the distal surface, as shown in FIGS. 4-5, for ease of separation of the flaps. Internal camming surface 93 may be integral with the protective sheath 92, as by molding or an extrusion or other forming technique.

Figure 9D:
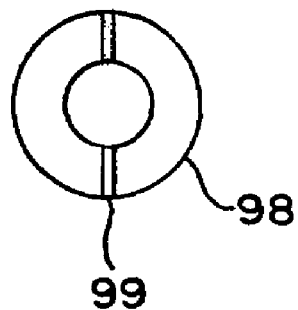

Alternately, as shown in the cross sectional view of FIG. 9c and the plan view of FIG. 9d, the camming surface 96 may be formed separately, as by molding or machining. The surface may then be assembled to the inner surface of protective sheath 95, for example, by plastic welding, sonic welding, or an adhesive. As mentioned above, the camming surface is preferably used in conjunction with the penetrations in the distal surface of the protective sheath, so that flaps 94 are easily released from penetrations of cuts 97. In this embodiment, as shown in the plan view of FIG. 9d, the camming surface may have two voids 99, forming two portions 98, the voids preferably aligned with penetrations 97. Other embodiments of camming surfaces may have more than two voids.

FIGS. 10 and 11 include a two catheter system that may be used for cellular transfer or other procedures. The first catheter 70 includes a proximal portion 72 and a distal portion 74. The proximal portion may include a hub 75 for interfacing with a syringe for implanting cellular material. The catheter may also include a central lumen 73 and an echogenic tip 76, preferably made of stainless steel, for detecting the distal end via ultrasound. The catheter may also have markings 78 at the proximal or distal end indicating a position of the catheter to implantation personnel. The interior of central lumen 78 may be coated with a lubricious material 79 to facilitate transfer of cellular material or for other purposes. The catheter includes a male snap fit feature 77 on proximal portion 72 for interfacing with a second catheter.

Second catheter 80 is depicted in FIG. 11. The second catheter may be considered to be a guide catheter or a protective sheath. Second catheter 80 includes a proximal portion 82, a distal portion 84, and a hub 85, the distal portion enclosed and having a partially open or scored end 86. Second catheter 80 may also have markings 88 at the proximal end to guide operating personnel. There may be a female snap on feature 87 on hub 85 at the proximal end for interfacing with first catheter 70. For instance, when transferring cellular material, a physician may advance both catheters to a certain point, and then retract the second catheter, causing the first catheter to protrude through scored or open end 86. The first catheter may then transfer cellular material, or may sample a body fluid for removal outside the patient's body.

FIGS. 12-16 concern details of the snap fit features useful in medical devices. FIG. 12 depicts a first inner catheter 100 with a male snap fit feature 101 on an external surface. In this instance, second catheter 102 has been assembled to first catheter 100 using a female snap fit feature 104 that engages an edge 108 of male snap fit feature 101. Second catheter 102 also includes a male snap fit feature 103 on an external surface. Third catheter 105 has been assembled to second catheter 102 using female snap on feature 107. Female snap on feature 107 of the third catheter engages an opposing edge 109 of male snap on feature 103 of the second catheter. Note that a male snap on feature necessarily is on an external surface while a female snap fit feature necessarily is on an inner surface.

Figure 8:
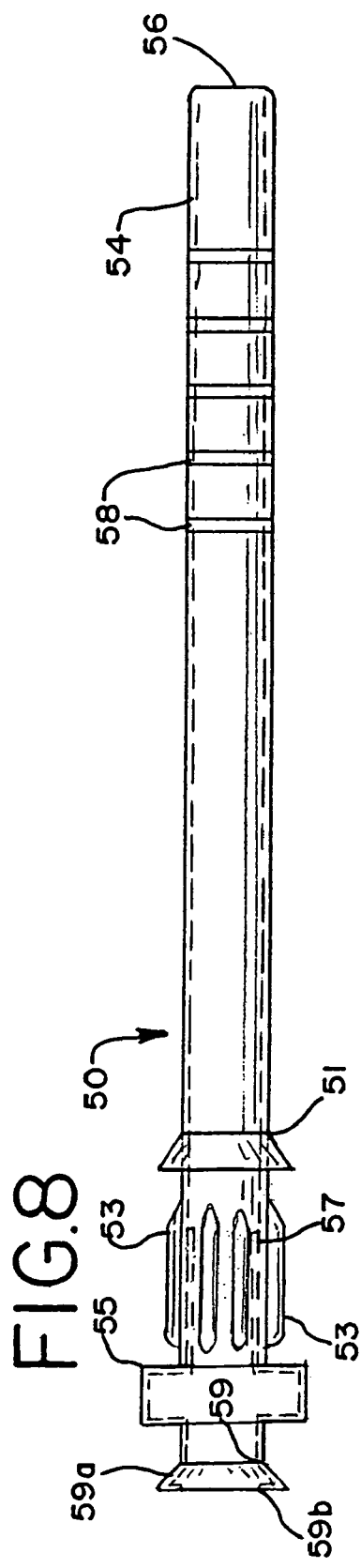
FIG. 8 depicts an alternative embodiment of a guide catheter with both male and female snap on features.

Male snap on features may comprise edges formed at right angles to an axis of the component of which they form a part, as depicted in FIGS. 7, 8, and 10. The edges may also be formed at other angles, such as an acute angle (less than 90°) or an obtuse angle (greater than 90°) as shown in FIGS. 13-14. In FIG. 13, catheter 110 has a male snap on feature 111 formed on an external surface at angle A, which is slightly less than 90°. In FIG. 14, catheter 120 has a male snap of feature 121 formed at a somewhat obtuse angle B. A mating female snap on feature may become disengaged more easily from catheter 120, while catheter 110 will disengage less easily, as the female snap on feature will tend to catch on upper surface 112.

Female snap on features are depicted in FIGS. 15 and 16. As noted above, female snap on features are necessarily formed on an internal surface. In catheter 130, female snap on feature 131 is formed with an upper lip or upper engagement surface 132 and a void 133. Lip 132 is meant to engage with a mating edge of a male snap fit, while void 133 is meant to accommodate the male snap fit feature. As depicted in FIG. 15, lip 132 may be formed perpendicular to the length of catheter 130. FIG. 16 depicts an alternate embodiment of a catheter 140 with a female snap fit feature 141. Snap fit feature 141 comprises a lip or engagement surface 142 and a void 143 for accommodating a mating male snap fit feature. The lip need not be formed to any exacting specification. All that is necessary is that the female feature be sufficiently deformable so that it is able to move over the male snap on feature and then engage the male feature with a void. In some cases, the female snap on feature may be formed by using a flaring tool and forming and cutting a thermoplastic catheter so that it has the void and lip required for a basic snap fit function.

Unrelated snap fits, for instance in automotive or mechanical assembly, may positively prevent movement or disassembly without machining away the outer part. In medical use, the snap on features should be designed so that catheters engage positively for the convenience of the physician or clinician, but so that the catheters can be removed from each other with a modicum of effort. In some embodiments, snap-fit features made with elastomeric or plastic materials with a durometer from Shore D 50-95 in the protective sheath (female portion) has worked well, and particularly in the range of 60-70 Shore D. In one embodiment, the outer protective sheath works well with a harder material, such as high density polyethylene. The guide catheter and delivery catheter are preferably made from softer materials, for instance, materials about Shore A durometer 80.

In addition, it has been found that thicknesses in the female snap-fit parts from about 0.005 inches to about 0.025 inches work well, and particularly from about 0.010 to 0.020 inches. The male portion of the snap fit works well so long as it is designed to mate with the female portion. The combination of a relatively soft, deformable inner or male portion, Shore A 80-Shore D 50, works well with a harder outer or female portion, preferably Shore D 50-95.

Figure 17:
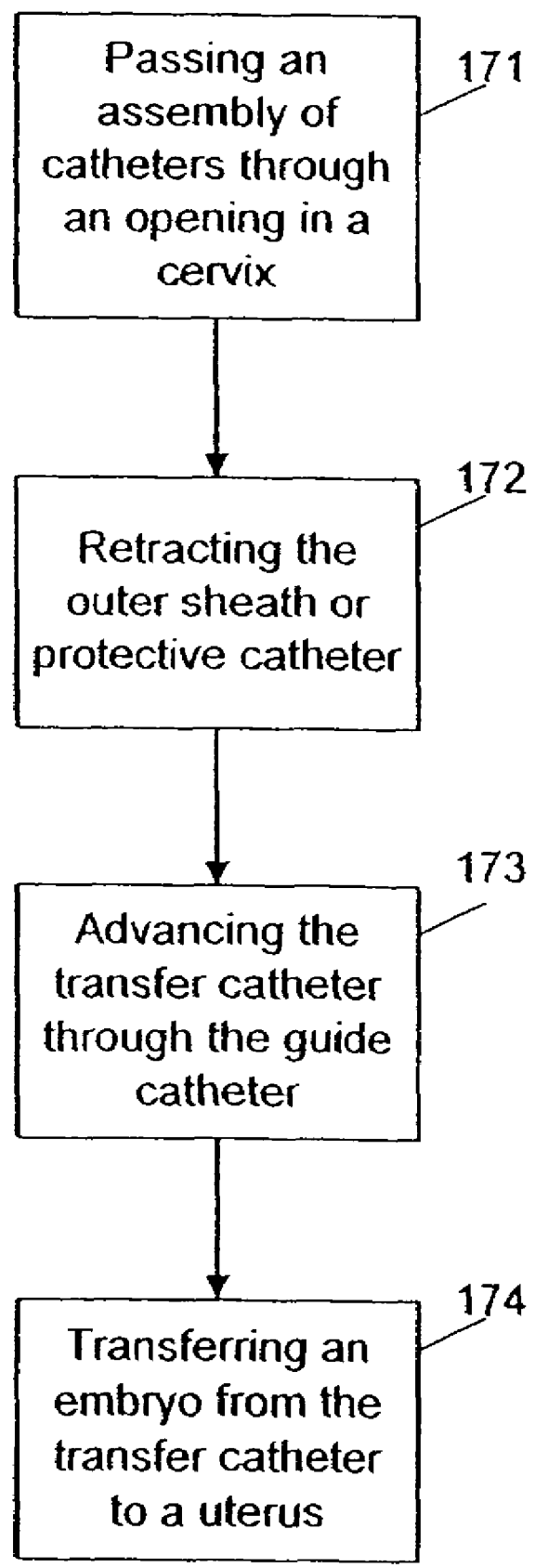
FIG. 17 depicts a method of using a transfer and guide catheter with a protective sheath.

As discussed above, the protective sheath, the guide catheter, and the transfer catheter may be used to implant an embryo or other cellular material. Another embodiment of the invention is a method of using an embryo transfer system to implant an embryo, or other cellular material in a uterus. FIG. 17 is a flowchart depicting one method. In this method, a first step is to pass 171 an assembly including a protective catheter or outer sheath, a guide catheter and a transfer catheter through an opening in a cervix. The protective catheter or sheath is then retracted 172 and may be snap fit onto the guide catheter. The transfer catheter is then passed through the guide catheter 173, exposing the transfer catheter to the uterus. The method then includes transferring an embryo or other cellular material from the transfer catheter to the uterus 174. The transfer is preferably accomplished by fluid pressure, using a small amount of fluid.

Figure 18:
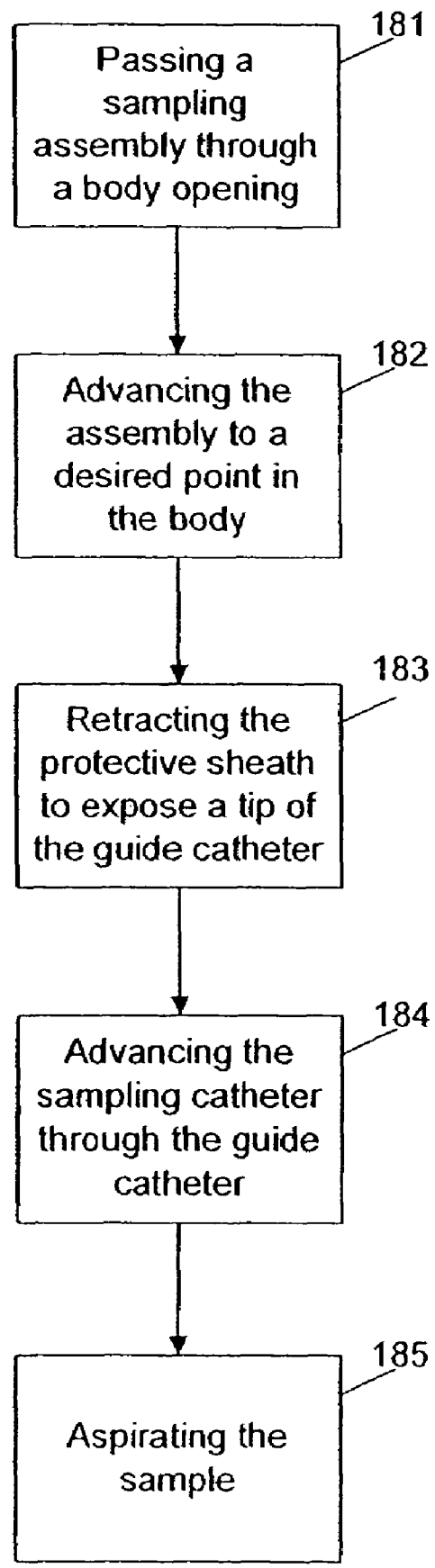
FIG. 18 depicts a method of using a sampling assembly to collect a sample from within a body.

The assembly discussed above for transferring cellular material may also be used to collect samples from within a person's body. In this embodiment, a sampling assembly would include a protective sheath on the outside, a guide catheter within the protective sheath, and a sampling catheter rather than a delivery catheter. A method of using the sampling assembly is depicted in FIG. 18. The first step 181 of the method is to pass the sampling assembly through an opening, such as a body orifice. The opening may be a natural body orifice, or may be a surgically-provided opening in the body. The sampling assembly is then advanced 182 to the desired point in the body. The protective sheath prevents contamination of the sampling catheter and the guide catheter from other body tissues and fluids that are not desired for sampling. The protective sheath is then retracted 183 to expose the tip of the guide catheter. The sampling catheter is then advanced 184 through the guide catheter to the region or point of interest. The sample is then aspirated 185 into the sampling catheter. The sample may be aspirated to a point outside the body, or the sample may be aspirated into the sampling catheter, with the sampling catheter then withdrawn into the guide catheter or the protective sheath, or both, before withdrawal from the body. The sample is then analyzed for diagnosis or treatment of the patient.

It should be understood that the use of snap on features in catheters is not limited to cellular material or embryo transfer applications. Thus, catheters with snap on features may desirably be used in any of a number of other applications, such as for insemination and for collecting samples of body fluids. The snap-fit features allow for interchangeability of catheters of varying lengths with other catheters of the same or varying length. The physician or clinician is able to assemble a kit using a first catheter of one length and a second catheter of a second length, so long as one of the first and second catheters has a male snap on feature and the other catheter has a matching female snap on feature. Thus, there is less need to inventory a large number of sealed and sterilized kits, each containing a particular combination of catheter lengths.

The details of the construction or composition of the various elements of the cellular transfer catheter not otherwise disclosed are not believed to be critical to the achievement of the advantages of the present invention, so long as the elements possess the strength or flexibility or softness needed for them to perform as disclosed. The selection of such details of construction is believed to be well within the ability of one of even rudimentary skills in this area, in view of the present disclosure, and are within the spirit of the invention and the scope of the claims. It will be understood that no limitation of the scope of the invention is intended by the above description and drawings, which is defined by the claims below.

What is claimed is:

1. A catheter system, comprising:
   a first relatively flexible catheter having a first snap on feature; and
   a second relatively flexible catheter, wherein the first and second catheters are configured to be aligned with the first catheter disposed within a lumen of the second catheter for a substantial portion of the length of each of the first and second catheter when the first snap on feature engages the second catheter,
   wherein the first snap on feature is defined continuously around an entire outer circumference of the first catheter along a portion of a length of the first catheter.

2. The system of claim 1, wherein the second catheter is configured to receive the snap on feature of the first catheter.

3. The system of claim 1, wherein the first catheter snap on feature fits within a feature on the second catheter.

4. The system of claim 1, wherein at least one of the first and second catheters has a recess to form or accept the snap on feature.

5. The system of claim 1, wherein the first catheter is a delivery catheter and the second catheter is a guide catheter configured to receive the snap on feature.

6. The system of claim 1, wherein the first catheter is a guide catheter and the second catheter is a protective sheath configured to receive the snap on feature.

7. The system of claim 1, wherein the first catheter is a guide catheter and the second catheter is a protective sheath configured to receive the first snap on feature on an external surface of the guide catheter, the guide catheter further comprising a second snap on feature on an internal surface of the guide catheter, and further comprising a delivery catheter configured to receive the second snap on feature of the guide catheter.

8. The system of claim 7, wherein the protective sheath, the guide catheter, and the delivery catheter are each configured to extend coaxially for a substantial portion of the length of each of the protective sheath, guide catheter, and delivery catheter when the first snap on feature engages the guide catheter, and when the second snap on feature engages the delivery catheter.

9. The system of claim 7, wherein the delivery catheter comprises a cylindrical feature with an edge facing a proximal direction that engages the second snap on feature.

10. The system of claim 1, wherein the first catheter is an insemination catheter and the second catheter is a guiding catheter configured to receive the snap on feature.

11. The system of claim 1, wherein the first catheter is an embryo transfer catheter and the snap fit feature is a cylindrical feature with an edge facing in a proximal direction.

12. The system of claim 11, wherein the second catheter is a guide catheter and further comprises a second snap fit feature defined therein and configured to receive the first snap fit feature.

13. The system of claim 12, wherein the second snap fit feature defines a void to receive the first snap fit feature, and a proximally facing edge for mating with the edge of the first snap fit feature.

14. The system of claim 12, wherein the second catheter further comprises a male third snap fit feature defined upon an outer surface of the second catheter.

15. The system of claim 14, further comprising a third catheter configured to slidably receive the second catheter within an inner volume of the third catheter, wherein the third catheter comprises a female fourth snap fit feature configured to receive the third snap fit feature therein.

16. The cellular transfer system of claim 1, wherein,
   the first catheter is a transfer catheter;
   the second catheter is a guide catheter for holding and guiding the transfer catheter; and
   further comprising a protective sheath outside the guide catheter, the protective sheath comprising at least one of break-through and peel-away features, wherein the protective sheath splits into at least two portions when the protective sheath is withdrawn or the guide catheter is advanced through the protective sheath.

17. The cellular transfer system of claim 16, wherein the break-through and peel-away feature comprise at least one of perforations, penetrations, and scores through the protective sheath.

18. The cellular transfer system of claim 16, wherein at least the protective sheath is made from a fluoropolymer material.

19. The cellular transfer system of claim 16, wherein the transfer catheter has a transfer volume of from about 5 λl to about 15 λl.

20. The cellular transfer system of claim 16, further comprising a camming surface on the protective sheath or the guide catheter.

* * * * *

UNITED STATES PATENT AND TRADEMARK OFFICE
CERTIFICATE OF CORRECTION

PATENT NO. : 7,637,904 B2 Page 1 of 1
APPLICATION NO. : 10/741918
DATED : December 29, 2009
INVENTOR(S) : Troy W. Wingler et al.

It is certified that error appears in the above-identified patent and that said Letters Patent is hereby corrected as shown below:

<u>In the Claims</u>

In column 12, claim 19, lines 53-54, after "transfer volume of from about" replace "5 λI to about 15 λI." with --5 μl to about 15 μl.--.

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,637,904 B2 Page 1 of 1
APPLICATION NO. : 10/741918
DATED : December 29, 2009
INVENTOR(S) : Troy W. Wingler et al.

It is certified that error appears in the above-identified patent and that said Letters Patent is hereby corrected as shown below:

On the Title Page

Item (73), insert --; Sabin Corporation, Bloomington, IN (US)--.

Signed and Sealed this

Seventeenth Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,637,904 B2  Page 1 of 1
APPLICATION NO. : 10/741918
DATED : December 29, 2009
INVENTOR(S) : Wingler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1384 days.

Signed and Sealed this

Ninth Day of November, 2010

David J. Kappos
*Director of the United States Patent and Trademark Office*